(12) United States Patent
Tracey et al.

(10) Patent No.: US 8,715,658 B2
(45) Date of Patent: May 6, 2014

(54) METHODS FOR TREATING CONDITIONS MEDIATED BY THE INFLAMMATORY CYTOKINE CASCADE USING GAPDH INHIBITORS

(75) Inventors: Kevin Tracey, Old Greenwich, CT (US); William Parrish, Hudson, MA (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 0 days.

(21) Appl. No.: 13/391,465

(22) PCT Filed: Aug. 17, 2010

(86) PCT No.: PCT/US2010/002258
§ 371 (c)(1),
(2), (4) Date: Apr. 27, 2012

(87) PCT Pub. No.: WO2011/025524
PCT Pub. Date: Mar. 3, 2011

(65) Prior Publication Data
US 2012/0219546 A1    Aug. 30, 2012

Related U.S. Application Data

(60) Provisional application No. 61/275,199, filed on Aug. 26, 2009.

(51) Int. Cl.
*A61K 39/395* (2006.01)
*C07K 16/40* (2006.01)
*A61K 38/02* (2006.01)

(52) U.S. Cl.
USPC ............ 424/130.1; 424/133.1; 424/146.1; 424/158.1; 514/1.4; 514/2.1; 530/387.1; 530/387.3; 530/388.15; 530/388.26; 530/389.1

(58) Field of Classification Search
None
See application file for complete search history.

(56) References Cited

U.S. PATENT DOCUMENTS

| 6,521,743 | B1 | 2/2003 | Ishitani et al. |
| 2003/0092085 | A1 | 5/2003 | Ishitani et al. |
| 2005/0125044 | A1 | 6/2005 | Tracey |
| 2006/0293325 | A1 | 12/2006 | Chang et al. |
| 2009/0248097 | A1 | 10/2009 | Tracey et al. |

OTHER PUBLICATIONS

Stedman online Dictionary: Paralysis, Mar. 4, 2013.*
Stedman online Dictionary: Asthma, Mar. 4, 2013.*
Stedman online Dictionary:: Celiac disease, Mar. 4, 2013.*
Stedman online Dictionary: Paralysis, Feb. 23, 2013.*
Stedman online Dictionary: Asthma, Feb. 23, 2013.*
Stedman online Dictionary:: Celiac disease, Feb. 23, 2013.*
Mautes et al, Journal of the American Physical therapy Association, 2000, vol. 80, pp. 673-687.*
Communication Supplementary European Search Report issued by the European Patent Office dated Jan. 30, 2013 in connection with European Patent Application No. 10812427.2, 10 pages.
Gil M L et al., entitled "Evaluation of the usefulness of anti-glyceraldehyde-3-phosphate dehydrogenase antibodies as a treatment for invasive candidiasis in a murine model," Antonie van Leeuwenhock (2006) 89:345-350.
Fugier E et al., entitled "The Glyceraldehyde-3-Phosphate Dehydrogenase and the Small GTPase Rab 2 Are Crucial for Brucella Replication," PLoS Pathogens, vol. 5, Issue 6, Jun. 2009, pp. 1-10.
Pereira J M et al., entitled "Anacardic acid derivatives as inhibitors of glyceraldehyde-3-phosphate dehyrogenase from Trypanosoma cruzi," Bioorganic & Medicinal Chemistry 16 (2008) 8889-8895.
PCT International Search Report dated Sep. 29, 2010 in connection with PCT International Patent Application No. PCT/US2010/02258, 5 pages.
PCT Written Opinion of the International Searching Authority dated Sep. 29, 2010 in connection with PCT International Patent Application No. PCT/US2010/02258, 5 pages.

\* cited by examiner

*Primary Examiner* — Bridget E Bunner
*Assistant Examiner* — Fozia Hamud
(74) *Attorney, Agent, or Firm* — Amster, Rothstein & Ebenstein LLP

(57) ABSTRACT

The present invention is directed to a method of treating a subject at risk for or having a condition mediated by an inflammatory cytokine cascade comprising administering to the subject an amount of a GAPDH inhibitor effective to treat the subject at risk for or having a condition mediated by an inflammatory cytokine cascade.

16 Claims, 17 Drawing Sheets

Figure 1. RAW264.7 cells challenged with LPS exhibit delayed release of F350

Figure 2. F350 treatment elicits TNF response from RAW264.7 cells

Figure 3. Macrophages deficient in the TLR4 receptor do not mount a significant response to F350

Figure 4. F350 activates inflammatory signaling pathways through the TLR4 receptor in RAW264.7 macrophage-like cells Figure 5. The α-F350 #4418 polyclonal antibody neutralizes F350 in human whole blood assays

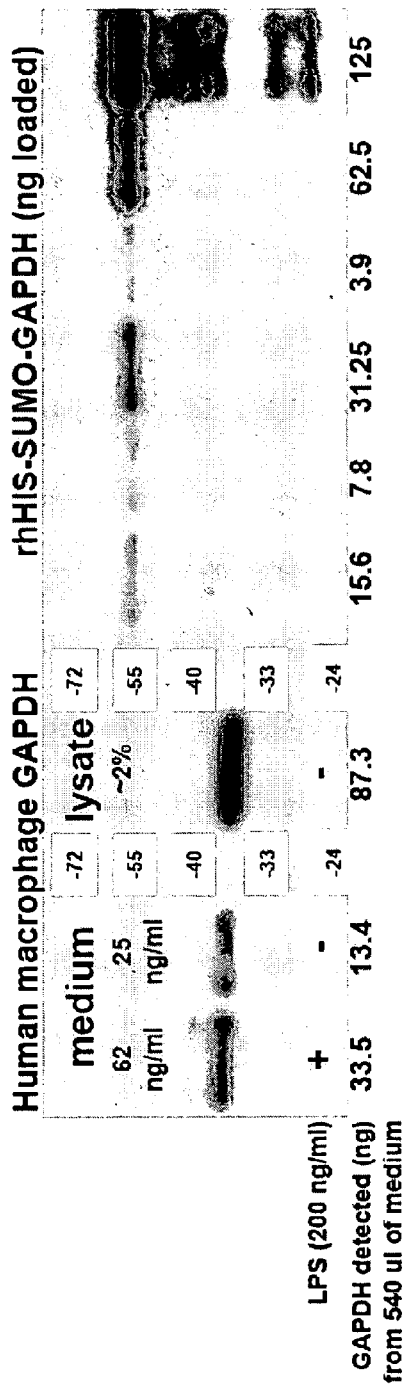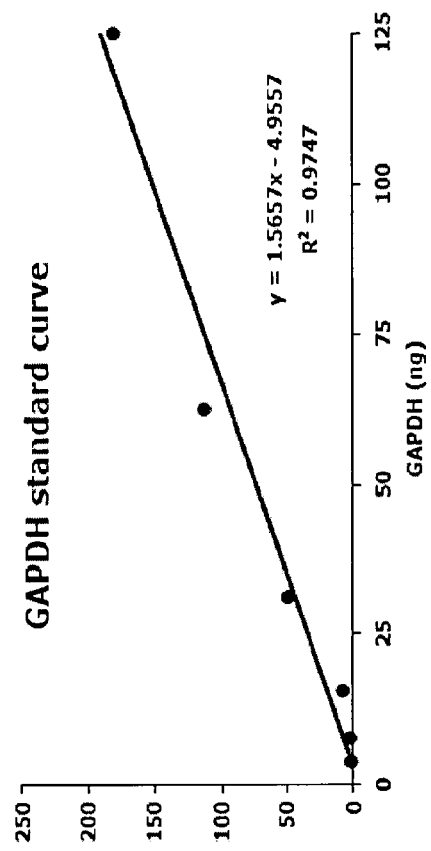
FIG. 17

US 8,715,658 B2

METHODS FOR TREATING CONDITIONS MEDIATED BY THE INFLAMMATORY CYTOKINE CASCADE USING GAPDH INHIBITORS

CROSS-REFERENCE TO RELATED APPLICATIONS

This application is a U.S. national stage entry under 35 U.S.C. §371 of PCT International Patent Application No. PCT/US2010/002258, filed Aug. 17, 2010, and claims priority to U.S. Provisional Patent Application No. 61/275,199, filed Aug. 26, 2009, the contents of which are incorporated herein by reference in their entirety.

FIELD OF THE INVENTION

The present invention relates to the treatment of inflammatory disorders using GAPDH inhibitors.

BACKGROUND OF THE INVENTION

Sepsis is clinically characterized as a systemic inflammatory response to infection, but it can also arise from trauma or injury [1-5]. Sepsis is clinically characterized as a systemic inflammatory response to infection, but it can also arise from trauma or injury [1-5]. Sepsis is a serious medical problem and scientific challenge with a significant unmet need, as it is the leading cause of death among patients in Intensive Care Units (ICU) worldwide. Mortality rates range from 20% for sepsis, to 40% for severe sepsis, and >60% for septic shock [2-4]. Current therapies target the symptoms of sepsis and are geared to support cardiovascular and respiratory function, but they do not specifically address the underlying causes of the inflammatory disease, which involves a dysregulated or poorly balanced innate inflammatory response [1, 4, 10, 12]. The overall lack of improvement in sepsis survival rates, despite significant advances in supportive intensive care, indicates an unmet need in effective target-directed anti-sepsis therapies.

Sepsis is caused by the loss of homeostatic balance during the innate immune response to infection or injury [1, 2]. The innate immune response is driven primarily by signaling molecules collectively referred to as cytokines, which are used by cells of the immune system to communicate the integrity of the body's barriers to the environment. Cytokines are normally produced by immune cells in response to pathogen-associated molecules (PAMPs) or damage-associated molecules (DAMPs), and activate other immune cells to increase the body's immune response. There are two main classes of clinically relevant cytokines: pro-inflammatory mediators that activate and amplify inflammation and anti-inflammatory mediators that impede and balance the inflammatory response. A predominant belief amongst immunologists is that an unrestrained pro-inflammatory mediator cascade causes disease [1, 2, 4-12]. The dysregulated sequence of pro-inflammatory cytokines leading to disease has been referred to as a "cytokine storm" [13] or "inflammatory cascade" [14], as one cytokine typically leads to the production of multiple other cytokines to reinforce and amplify the immune response.

Pro-inflammatory mediators can be further broken down into two subgroups: early mediators and late mediators [1, 2, 19, 20]. Early mediators (tumor-necrosis factor, interleukin-1, interleukin-6, etc.) are not sufficient therapeutic targets for re-establishing homeostatic balance because they are resolved within the time frame of a patient's travel to a clinic to receive medical attention [1,10-12, 18, 19]. Conversely, late mediators can be therapeutically targeted as they fall later in the "inflammatory cascade," after a patient has realized that he or she has fallen ill. A promising example of targeting a late mediator for therapeutic benefit comes with high mobility group box 1 (HMGB1) [2,10-12, 15-20].

HMGB1 is a powerful late-acting cytokine that plays an important role in the pathogenesis of many inflammatory diseases. Blockade of the cytokine activity of HMGB1 through a variety of different methods improves the outcome in animal models of sepsis, rheumatoid arthritis, and other inflammatory diseases [15, 16]. However, HMGB1 also has key roles in promoting wound healing and the resolution of inflammation, which potentially confounds its value as a therapeutic target [15, 17]. Therefore, there has been a need to seek out other late-acting inflammatory cytokines with potentially fewer pleiotropic effects as therapeutic targets in inflammatory disease.

SUMMARY OF THE INVENTION

The present invention is directed to a method of treating a subject at risk for or having a condition mediated by an inflammatory cytokine cascade comprising administering to the subject an amount of a GAPDH inhibitor effective to treat the subject at risk for or having a condition mediated by an inflammatory cytokine cascade.

The present invention is also directed to method for determining whether a compound is potentially effective in modulating a condition mediated by an inflammatory cytokine, said method comprising contacting a candidate compound with GAPDH under conditions permitting the candidate compound to form a complex with GAPDH, wherein the formation of a complex indicates the candidate compound is potentially effective in modulating a condition mediated by an inflammatory cytokine.

In addition, the present invention is directed to the of a GAPDH inhibitor for treating a subject at risk for or having a condition mediated by an inflammatory cytokine.

The present invention is further directed to the use of a GAPDH inhibitor for the preparation of a medicament for treating a subject at risk for or having a condition mediated by an inflammatory cytokine.

Additional objects of the invention will be apparent from the description which follows.

BRIEF DESCRIPTION OF THE FIGURES

FIG. 17 shows a semi-quantitative western blot analysis of GAPDH release from human macrophages.

DETAILED DESCRIPTION OF THE INVENTION

Figure 1:
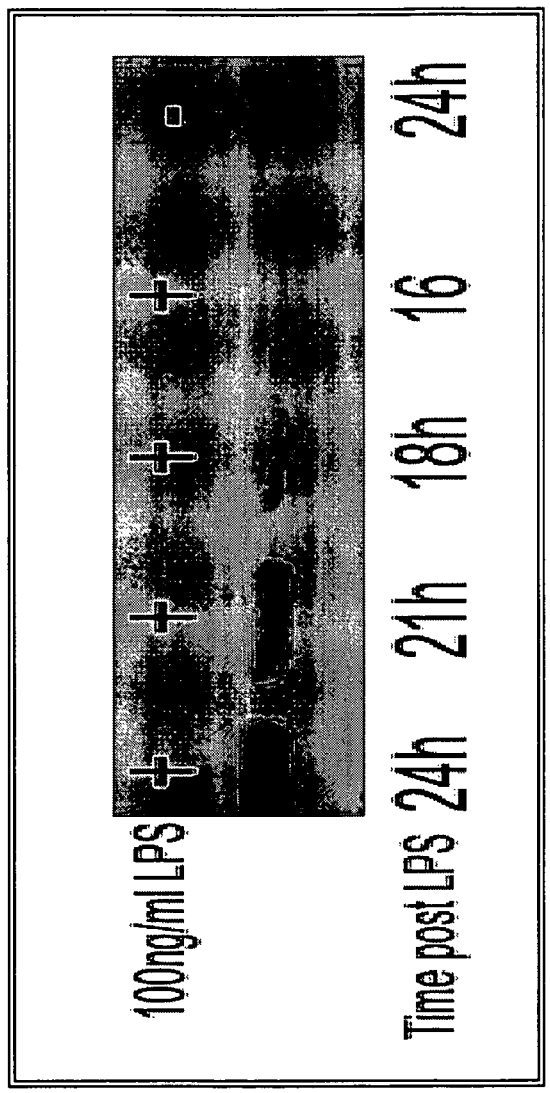
FIG. 1 shows that RAW264.7 cells challenged with LPS exhibit delayed release of GAPDH (i.e., denoted as F350 in the figure).

As discussed above, the present invention is directed to a method of treating a subject at risk for or having a condition mediated by an inflammatory cytokine cascade comprising administering to the subject an amount of a GAPDH inhibitor effective to treat the subject at risk for or having a condition mediated by an inflammatory cytokine cascade. In accordance with the method of the present invention, if the subject has a condition mediated by an inflammatory cytokine cascade, the condition is treated by the administration of a therapeutically effective amount of the GAPDH inhibitor. If the subject is a risk for a condition mediated by an inflammatory cytokine cascade, the subject is preferably administered a prophylatically effective amount of the GAPDH inhibitor. As used herein, a "therapeutically effective amount" is an amount effective to treat, attenuate or modulate a condition mediated by an inflammatory cytokine cascade. As used herein, a "prophylatically effective amount" is an amount effective to prevent or at the very least reduce the severity of a condition mediated by an inflammatory cytokine cascade in a patient at risk for developing a condition mediated by an inflammatory cytokine cascade.

As used herein, a "condition mediated by an inflammatory cytokine cascade" is a condition selected from the group consisting of appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, a parastic infection, a bacterial infection, a viral infection, an autoimmune disease, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, coeliac disease, congestive heart failure, adult respiratory distress syndrome, meningitis, encephalitis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, Retier's syndrome, and Hodgkins disease.

In a preferred embodiment, a condition mediated by an inflammatory cytokine is a condition selected from the group consisting of appendicitis, peptic, gastric and duodenal ulcers, peritonitis, pancreatitis, ulcerative, pseudomembranous, acute and ischemic colitis, hepatitis, Crohn's disease, asthma, allergy, anaphylactic shock, organ ischemia, reperfusion injury, organ necrosis, hay fever, sepsis, septicemia, endotoxic shock, cachexia, septic abortion, disseminated bacteremia, burns, coeliac disease, congestive heart failure, adult respiratory distress syndrome, cerebral infarction, cerebral embolism, spinal cord injury, paralysis, allograft rejection and graft-versus-host disease. Most preferably, the condition mediated by an inflammatory cytokine is sepsis, septicemia or endotoxic shock.

In a preferred embodiment, the GAPDH inhibitor is an agent that comprises an antibody binding site that binds specifically to the GAPDH, for example an antibody (e.g., a polyclonal or monoclonal antibody), an Fab fragment or an $F(ab)_2$ fragment of an antibody. Such agents can be produced by well-known methods, and include engineered antigen binding molecules such as a chimeric antibody (U.S. Pat. Nos. 4,816,567 and 4,816,397, which are incorporated by reference), a humanized antibody (U.S. Pat. Nos. 5,693,762, 5,585,089 and 5,565,332, which are incorporated by reference), a single chain Fv (U.S. Pat. No. 4,946,778, which is incorporated by reference), a diabody, a triabody, a tetrabody, a Fab conjugate (e.g., dimer and trimer), and a minibody. Non-limiting methods include: immunization of animals with GAPDH (or fragments thereof), followed by isolation of anti-GAPDH antibodies from serum or production of anti-GAPDH monoclonal antibodies from hybridomas made by fusion of spenocytes with myeloma cells; or phage display or other recombinant methods. Preferably, the monoclonal antibody is chosen or adapted to match the species to be treated. For treatment of humans, for example, the anti-GAPDH antibody (or antigen-binding fragment thereof) will be a human antibody or a humanized antibody. Such antigen-specific human or humanized monoclonal antibodies may be developed by a variety of methods well known in the art.

In other embodiments, the GAPDH inhibitor may be a GAPDH inhibitor known in the art such as the GAPDH inhibitors described in U.S. Publication No. 2006/0293325 A1, which is hereby incorporated by reference in its entirety.

If the GAPDH inhibitor is to be used for the treatment of a condition mediated by an inflammatory cytokine (or the treatment of a subject at risk for a condition mediated by an inflammatory cytokine), it is within the confines of the present invention that the GAPDH can be used for the preparation of a medicament in which the GAPDH inhibitor is formulated in a pharmaceutically acceptable carrier in unit dosage form. In this regard, pharmaceutical compositions useful for these embodiments can be formulated without undue experimentation for administration to a mammal, including humans, as appropriate for the desired mode of administration. Additionally, proper dosages of the compositions can be determined without undue experimentation using standard dose-response protocols.

For example, pharmaceutical compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like. Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

Pharmaceutical compositions useful for the present invention can also be administered parenterally such as, for example, by intravenous, intramuscular, intrathecal or subcutaneous injection. Parenteral administration can be accomplished by incorporating the compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

The present invention also includes nasally administering to the mammal the GAPDH inhibitor formulated in a carrier suitable for nasal administration. As used herein, nasally administering or nasal administration includes administering the composition to the mucous membranes of the nasal passage or nasal cavity of the patient. As used herein, pharmaceutical compositions for nasal administration of a composition include therapeutically effective amounts of GAPDH inhibitor formulated in a composition prepared by well-known methods to be administered, for example, as a nasal spray, nasal drop, suspension, gel, ointment, cream or powder. Administration of the composition may also take place using a nasal tampon or nasal sponge.

It is anticipated that, for many embodiments, it would be desired that the GAPDH inhibitor be administered parenterally, preferably, intravenously, to introduce the GAPDH inhibitor into the bloodstream as quickly as possible, to achieve the maximum anti-inflammatory effect.

The present invention is also directed to a method for determining whether a compound is potentially effective in modulating a condition mediated by an inflammatory cytokine. The method comprises the steps of contacting a candidate compound with GAPDH under conditions permitting the candidate compound to form a complex with GAPDH. The formation of a complex indicates the candidate compound is potentially effective in modulating a condition mediated by an inflammatory cytokine, and may be used for treating a condition mediated by an inflammatory cytokine or the treatment of a subject at risk for a condition mediated by an inflammatory cytokine. The contacting is performed using standard procedures known in the art.

With respect to screening for potential agents or compounds that are inhibitors of GAPDH, the condition mediated by an inflammatory cytokine is selected from the group consisting of appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, a parastic infection, a bacterial infection, a viral infection, an autoimmune disease, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, coeliac disease, congestive heart failure, adult respiratory distress syndrome, meningitis, encephalitis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, Retier's syndrome, and Hodgkins disease.

In the preferred embodiment, the condition mediated by an inflammatory cytokine for purposes of screening for GAPDH inhibitors is selected from the group consisting of appendicitis, peptic, gastric and duodenal ulcers, peritonitis, pancreatitis, ulcerative, pseudomembranous, acute and ischemic colitis, hepatitis, Crohn's disease, asthma, allergy, anaphylactic shock, organ ischemia, reperfusion injury, organ necrosis, hay fever, sepsis, septicemia, endotoxic shock, cachexia, septic abortion, disseminated bacteremia, burns, coeliac disease, congestive heart failure, adult respiratory distress syndrome, cerebral infarction, cerebral embolism, spinal cord injury, paralysis, allograft rejection and graft-versus-host disease. Most preferably, the condition mediated by an inflammatory cytokine for purposes of screening for GAPDH inhibitors is sepsis, septicemia or endotoxic shock.

This invention will be better understood from the Experimental Details which follow. However, one skilled in the art will readily appreciate that the specific methods and results discussed are merely illustrative of the invention as described more fully in the claims which follow thereafter.

Experimental Details

Methods

GAPDH was chosen for study as a candidate inflammatory cytokine because it has a high degree of evolutionary conservation, as a homolog of GAPDH has been identified in every kingdom and phylum studied. It was of particular interest because there is significant amino acid sequence identity shared between the human GAPDH homolog and the GAPDH homolog found in several bacteria including hemolytic *Escherichia coli, Salmonella typhii, Streptococcus pyogenes, Staphylococcus aureus, Neisseria meningitidis,* and others that cause human disease. The percent identity and percent similarity of the homolog of GAPDH found in selected species as compared with the human homolog of GAPDH is presented in Table 1 below.

TABLE 1

F350 is highly conserved through evolution

| Organism | % Identity | % Similarity |
| --- | --- | --- |
| Human | 100% | 100% |
| Escherichia coli | 66% | 90% |
| Salmonella typhii | 66% | 85% |
| Streptococcus pyogenes | 46% | 80% |
| Staphylococcus aureus | 45% | 77% |
| Neisseria meningitidis | 44% | 79% |

GAPDH Protein Sequence Alignments.

GAPDH protein sequences were obtained from the National Center for Biotechnology Information (NCBI) GAPDH protein sequence alignments database. Protein sequence alignments were conducted using the T-Coffee multiple sequence alignment server at the European Bioinformatics Institute (EBI) [ebi.ac.uk/Tools/t-coffee/index.html], and % identity and % similarity between GAPDH homologs were calculated based on the results of these alignments.

Cell Culture.

Murine macrophage-like RAW264.7 cells were obtained from the American Type Tissue collection (ATTC). The RAW264.7 cells were cultured in Dulbecco's Modified Essential Medium (DMEM) (Gibco) supplemented with 1% heat-inactivated fetal bovine serum (FBS) (BioWhittaker), and 2 mM L-glutamine, and 100 µg/ml penicillin and streptomycin (all from Sigma). Raw264.7 cultures were incubated at 37° C. under 5% $CO_2$. The cells were serum-deprived in 1% FBS medium for the purpose of slowing the cell cycle to synchronize the cell population. Serum deprivation of the cells also limits available growth factors, minimizing the level of intracellular signaling in pathways that lead to the activation of mitogen-activated protein (MAP) kinases. It is interesting to note that immune challenges such as bacterial endotoxin (LPS) also activate MAP kinases to generate inflammatory responses, and thus high levels of FBS would interfere with the detection of MAP kinase signals that are elicited by the specific immune challenges that this study investigates. RAW264.7 cells were used at approximately 70% confluence, and all treatments were carried out in serum-free Opti-MEM I medium.

Peritoneal macrophages harvested from Wildtype, Toll-like receptor (TLR) 2, TLR4, or Receptor for Advanced Glycation Endproducts (RAGE) deficient mice were resuspended in RPMI1640 medium (Gibco) supplemented with 10% FBS and 2 mM L-glutamine, and 100 µg/ml penicillin and streptomycin, and plated at $1\times10^6$ cells/well into 24-well Primaria tissue culture plates (Falcon). Cultures were maintained for 24 h at 37° C. under 5% $CO_2$. 30 minutes prior to experimentation, culture medium was replaced by serum free Opti-MEM I medium, and all treatments were conducted in serum free Opti-MEM I medium as described.

RAW264.7 Cells Challenged with LPS for GAPDH Production.

RAW264.7 cells at approximately 70% confluence were kept in serum-free Opti-MEM I (Gibco) for 20 minutes prior to treatments. Cells were challenged with 100 ng/ml LPS (Sigma) (sonicated for approximately 30 minutes prior to use) in a time-course consisting of four time points (24 hrs, 21 hrs, 18 hrs, and 16 hrs). The media samples were then transferred to tubes and the cells were lysed with M-cell lysis reagent (Sigma). BCA protein assays (Pierce) were conducted on cell lysates, and the results were used to standardize for the quantity of cells that contributed to the level of GAPDH that was detected in the medium by Western blot. Samples were resolved by sodium dodecyl sulfate polyacrylamide gel electrophoresis (SDS-PAGE) and gels were transferred onto polyvinylidene fluoride (PVDF) membranes (Biorad). The membranes were blocked in 5% milk for 2 hours and probed with IgG purified from rabbit antiserum directed against F350 at a dilution of 1:1000 in PBST for two hours. Bound anti-F350 antibody was detected with horseradish peroxidase (HRP)-conjugated goat anti-rabbit IgG (Abcam) diluted at 1:2000 in 2.5% milk for one hour. The blots were developed with enhanced chemiluminesence (ECL) reagents (Pierce) and visualized by exposing on high-sensitivity X-ray film (Kodak).

RAW264.7 Cells Challenged with GAPDH for Cytokine Elicitation.

RAW264.7 cells at approximately 70% confluence were kept in serum-free Opti-MEM I for 20 minutes prior to treatments. Cells were challenged with a concentration range of purified recombinant GAPDH (produced on site) to determine concentration-dependent responsiveness of inflammatory mediator production. The concentration range consisted of seven concentrations of GAPDH in a five-fold dilution series (50 µg/ml, 10 µg/ml, 2 µg/ml, 0.4 µg/ml, 0.08 µg/ml, 0.016 µg/ml, 0 µg/ml). Cells were incubated at 37° C. and 5% $CO_2$ for 4 hours (TNF). After treatment, the media was harvested and transferred to tubes, and M-cell lysis reagent was applied to the cells. A protein assay was conducted on the cell lysates, and this data was used to standardize for the quantity of cells contributing to TNF release. The media samples were applied to Enzyme-Linked ImmunoSorbent Assays (ELISA) directed against mouse-TNF (all ELISA reagents were obtained from R+D systems). These ELISA plates were set up and run according to the manufacturer's recommendations. Briefly, samples were incubated overnight in the ELISA plate on a rocker at 4° C. Plates were washed 3× with phosphate-buffered saline supplemented with 0.05% TWEEN-20, and detection antibody diluted at 1:2000 in 1% bovine serum albumin (BSA) was applied to the plates for 2 hours. The plates were washed again as above, and strepavidin-HRP diluted at 1:2000 in 1% BSA was applied to the plates for 15 minutes. The plates were washed again as above, then developed by applying substrate reagent to each well. Reactions were stopped by adding 2M $H_2SO_4$ when the standard curve had become obvious, typically 8 to 10 minutes.

RAW264.7 Cells Challenged with GAPDH or LPS for Signaling Pathway Activation.

RAW264.7 cells at approximately 70% confluence were kept in serum-free Opti-MEM I for 20 minutes prior to treatments. Cells were challenged with either GAPDH or LPS in a time-course with seven time points (180 min, 120 min, 60 min, 30 min, 15 min, and 0 min). The GAPDH treatment consisted of purified GAPDH diluted to 50 µg/ml in Opti-MEM I. The LPS treatment consisted of LPS (sonicated approximately 30 minutes before use) diluted to 20 ng/ml into Opti-MEM I. Treatments used for time-course experiments were incubated in a 37° C. water bath to maintain culture temperature between time points and sonicated for five minutes before use. Upon completion of the treatments, the plates were placed on ice, where the media was aspirated off the wells and immediately replaced with ice cold cell lysis buffer [M cell lysis reagent supplemented to 1% SDS, 0.1% NaN3, and HALT protease and phosphatase inhibitors (Pierce)]. When applied to the cells, the buffer forms a highly viscous solution that results from instantaneous and complete cell lysis. The lysates were scraped and the samples were transferred to tubes using 1 ml sterile syringes with a small gauge (26 g) needle. To homogenize the lysates, the samples were drawn into and out of the syringe approximately twenty times. The samples were then spun down in a microcentrifuge for 5 minutes at 14,000 revolutions per minute (rpm) and BCA protein assays were then conducted on homogenized lysates of challenged cells. Results from these protein assays were then used to standardize the level of protein loaded into each well of SDS-PAGE gels in a final volume of 40 µl. Gels were then transferred to PVDF membranes, which were then blocked in 5% milk for two hours. Membranes were then probed with specific antibodies directed against either nuclear factor of kappa light polypeptide gene enhancer in B-cells inhibitor, alpha (IκBα) or the activated forms of c-Jun N-terminal kinases (JNK) (Cell Signaling Technologies) that were diluted 1:1000 in PBST supplemented with 2.5% milk, and incubated overnight on a rocker at 4° C. Bound IκBα antibody was detected using a 1:2000 dilution of HRP-conjugated anti-mouse IgG in 2.5% milk; bound JNK antibody was detected using a 1:2000 dilution of HRP-conjugated anti-rabbit IgG in 2.5% milk. Membranes were incubated with this secondary antibody for two hours. The blots were developed using electrochemiluminescence ECL detection reagents, and visualized by exposure to X-ray film.

Neutralizing Activity of α-GAPDH #4418 Antibody in Human Whole Blood Assay.

Human whole blood was obtained from anonymous donors from the Long Island Blood Services. The blood was aliquotted into 48-well plates at 250 µl/well. Aliquots were then treated as indicated at 37° C. for four hours. Samples were centrifuged to separate plasma at 5000 rpm for five minutes at room temperature. TNF levels in the plasma were determined by ELISA as described above.

IgG from α-GAPDH #4418 antiserum was purified using protein A/G sepharose (Pierce). Purified IgG was used to test for the ability of α-GAPDH #4418 to neutralize GAPDH activity. Six conditions were tested: GAPDH (10 µg/ml) alone, GAPDH plus non-specific rabbit IgG (100 ug/ml), GAPDH plus α-GAPDH #4418 (100 ug/ml), α-GAPDH #4418 alone, non-specific rabbit IgG alone. The GAPDH plus α-GAPDH #4418 treatment was pre-incubated at room temperature for 30 minutes prior to applying the mixture to the whole blood.

Results and Discussion

RAW264.7 Cells Challenged with LPS Exhibit Delayed Release of GAPDH.

Cytokines are signaling molecules that are released by immune cells in response to immunological challenges such as infection or injury. Therefore, if an immune cell is activated by a bacterial endotoxin (LPS) challenge, it should mount a cytokine response. Therefore, we reasoned that if GAPDH functions as a cytokine, it should be elicited from LPS-activated macrophages in a time-dependent manner. To test this hypothesis, we challenged RAW264.7 cells with LPS and measured GAPDH in the culture supernatants at different time points. As shown in FIG. 1, our results indicate that GAPDH is released from activated immune cells in a time-dependent manner. We found that at 16 hours post LPS treatment, the culture supernatants showed no detectable GAPDH. At 18 hours post treatment, GAPDH became evident in the culture supernatants, and increased steadily to 24 hours post treatment. Unchallenged cells showed only trace amounts of GAPDH in the culture supernatants after 24 hours. This is significant because it indicates that GAPDH is released late from innate immune cells after LPS stimulation, and suggests that it may function as a late-acting cytokine during immune challenges, and in contrast to early cytokine mediators, could therefore serve as a therapeutic target during pathological inflammatory conditions.

GAPDH Treatment Elicits Cytokine Responses from RAW264.7 Macrophage-Like Cells.

Figure 2:
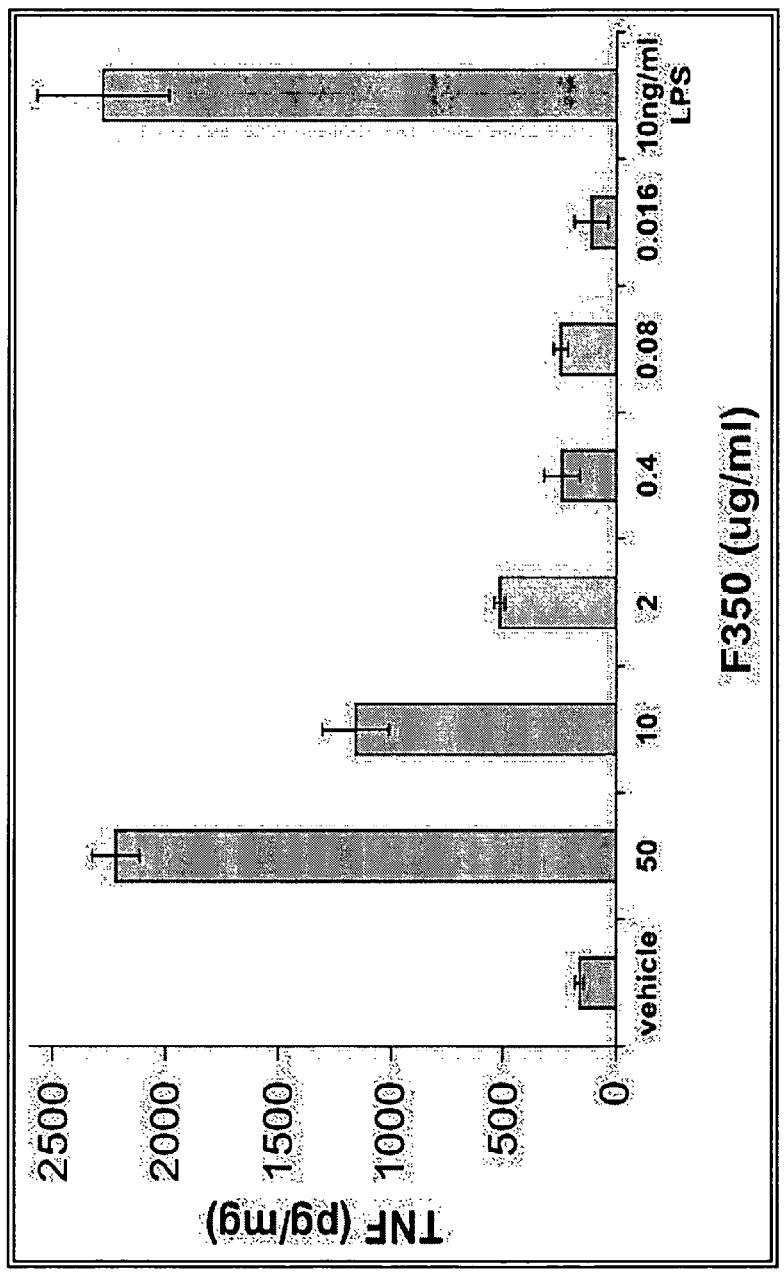
FIG. 2 shows that GAPDH treatment (i.e., F350 treatment in the figure) elicits TNF reponse from RAW264.7 cells.

Cytokines can mediate inflammatory disease. When an innate immune cell such as a macrophage encounters a pro-inflammatory cytokine, it responds by preparing to defend the body from foreign invaders. A key facet of this response is to alert more immune cells of the danger within the body by releasing more pro-inflammatory cytokines. Therefore, if GAPDH acts as an inflammatory cytokine, we hypothesized that macrophage-like RAW264.7 cells would produce tumor-necrosis factor (TNF), an early cytokine mediator of inflammatory disease [1, 2, 8, 9, 27], in response to GAPDH treatment. TNF is typically measured in significant amounts in the conditioned media of immune cells approximately 4 hours post treatment. We treated RAW264.7 cells with a five-fold dilution series (50 µg/ml-0.016 µg/ml) of purified recombinant human GAPDH, and subsequently measured the production and release of TNF into the medium by ELISA. Four hours after GAPDH treatment, we harvested the conditioned media and analyzed the levels of TNF by ELISA. These results were standardized to the amount of cellular protein in the cell lysates, and are presented in FIG. 2. GAPDH did indeed elicit TNF from RAW264.7 cells in a concentration-dependent manner. Cells treated with 50 µg/ml of GAPDH caused a TNF release of approximately 2250 pg/mg of cellular protein. This response was comparable to a treatment of 10 ng/ml LPS. Therefore, consistent with our hypothesis, GAPDH induces an innate immune response by prompting the cells to release pro-inflammatory mediators, indicating that it can function as a pro-inflammatory cytokine mediator of pathological inflammation.

GAPDH Activates Inflammatory Signaling Pathways Through the TLR4 Receptor in RAW264.7 Macrophage-Like Cell.

Innate immune cell activation results from the action of microbial products (PAMPS), endogenous danger signaling molecules (DAMPS), or inflammatory cytokines (TNF, HMGB1, IL-6, etc.), upon cell surface receptors that initiate intracellular signal transduction pathways culminating in inflammatory responses. There are many cell-surface receptors utilized by various cytokines, however Toll-like Receptors (TLRs) have a central role in recognizing PAMPs and DAMPs. TLRs and their downstream signaling components are highly conserved in metazoan evolution, as homologs are found in invertebrates as well as in vertebrates. In mammals, there are no less than 11 Toll-like receptors including TLR1-10 and the IL-1 receptor, each with a different capacity for recognizing classes of PAMPs or DAMPs [22-25]. For example, TLR1, 2, and 6 recognize acylated lipoproteins, TLR3 recognizes double-stranded RNA, TLR7 and 8 recognize single-stranded viral RNA, TLR9 recognizes bacterial CpG DNA, and TLR4 is the principle bacterial endotoxin (LPS) receptor. TLR2 and TLR4 have also been implicated in the recognition of various DAMPs including 70 kilodalton heat shock proteins (HSP70) and HMGB1 [22-26]. Because signaling proteins like HMGB1 also function as cytokines when secreted late in the inflammatory progression from activated immune cells, we reasoned that GAPDH might also activate inflammatory signaling either as a DAMP or as a cytokine, through TLR receptor-mediated pathways. Therefore, we tested whether GAPDH could activate inflammatory responses from macrophages that were taken from animals deficient for TLR2, TLR4, or the Receptor for Advanced Glycation End-products (RAGE), which has also been implicated in HMGB1 signaling activity.

Figure 3:
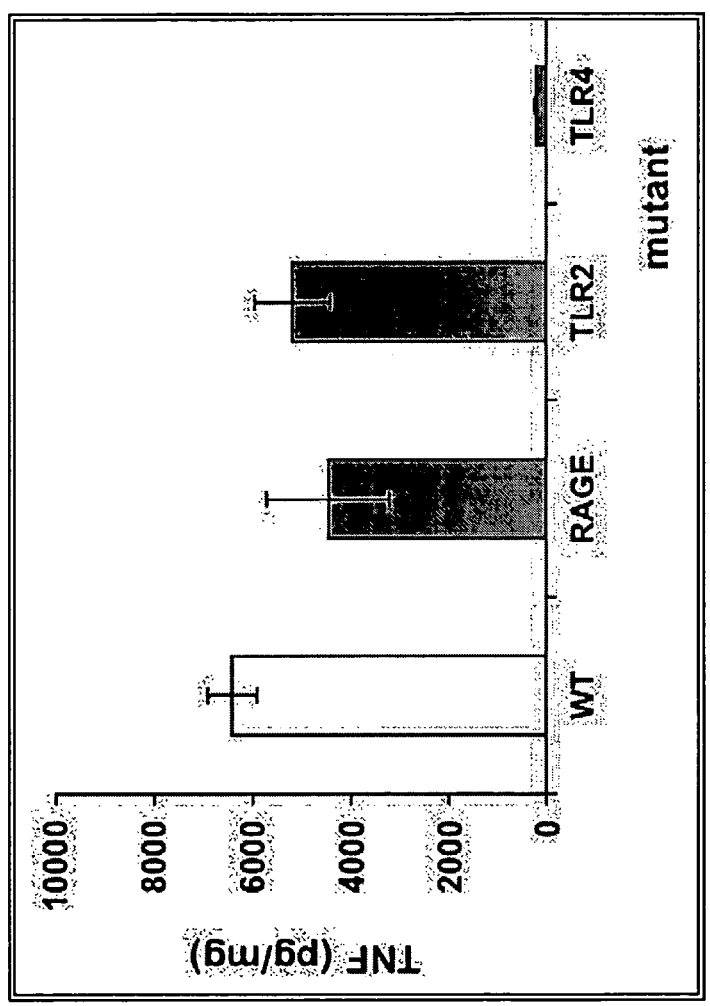
FIG. 3 shows that macrophages deficient in the TLR4 receptor do not mount a significant response to GAPDH (i.e., F350 in the figure).

As shown in FIG. 3, wild type macrophages responded robustly to treatment with 50 μg/ml GAPDH, releasing approximately 6000 pg TNF/mg cellular protein. Cells deficient for either RAGE or TLR2 also responded robustly to treatment with 50 μg/ml GAPDH, releasing approximately 4500 and 5000 pg TNF/mg cell protein, respectively, which was not significantly different than the wild type controls. In contrast, macrophages deficient for TLR4 did not mount a significant response to GAPDH. This data indicates that TLR4 is a principle cell surface receptor for GAPDH, and suggests that GAPDH elicits inflammatory responses from macrophages by activating TLR4 signaling pathways.

Consistent with TLR4 being the principle receptor through which GAPDH elicits inflammatory responses, we found that treatment of RAW264.7 cells with GAPDH activates signaling pathways that are downstream of TLR4. Activation of the TLR4 receptor signaling pathway leads to the activation of nuclear factor-kappa B (NF-κB). NF-κB is a transcription factor that is required for the production of inflammatory mediators in response to TLR activation [21]. NF-κB is maintained in an inactive form in the cytoplasm of immune cells by nuclear factor of kappa light polypeptide gene enhancer in B-cells inhibitor, alpha (IκBα). Therefore, IκBα degradation (readily detected as decreased levels in cell lysates by Western Blot analysis) corresponds directly to the activation of NF-κB. In addition, stimulation of the TLR4 receptor activates mitogen-activated protein (MAP) kinases, which are serine/threonine-specific protein kinases that respond to mitogens and regulate many cellular activities. One such MAP kinase is c-Jun N-terminal kinase (JNK), which is potently activated by TLR4 signaling [22, 24]. Therefore, we measured the ability of GAPDH treatment to cause the degradation of IκBα and the activation of JNK in RAW264.7 macrophage-like cells.

Figure 4:
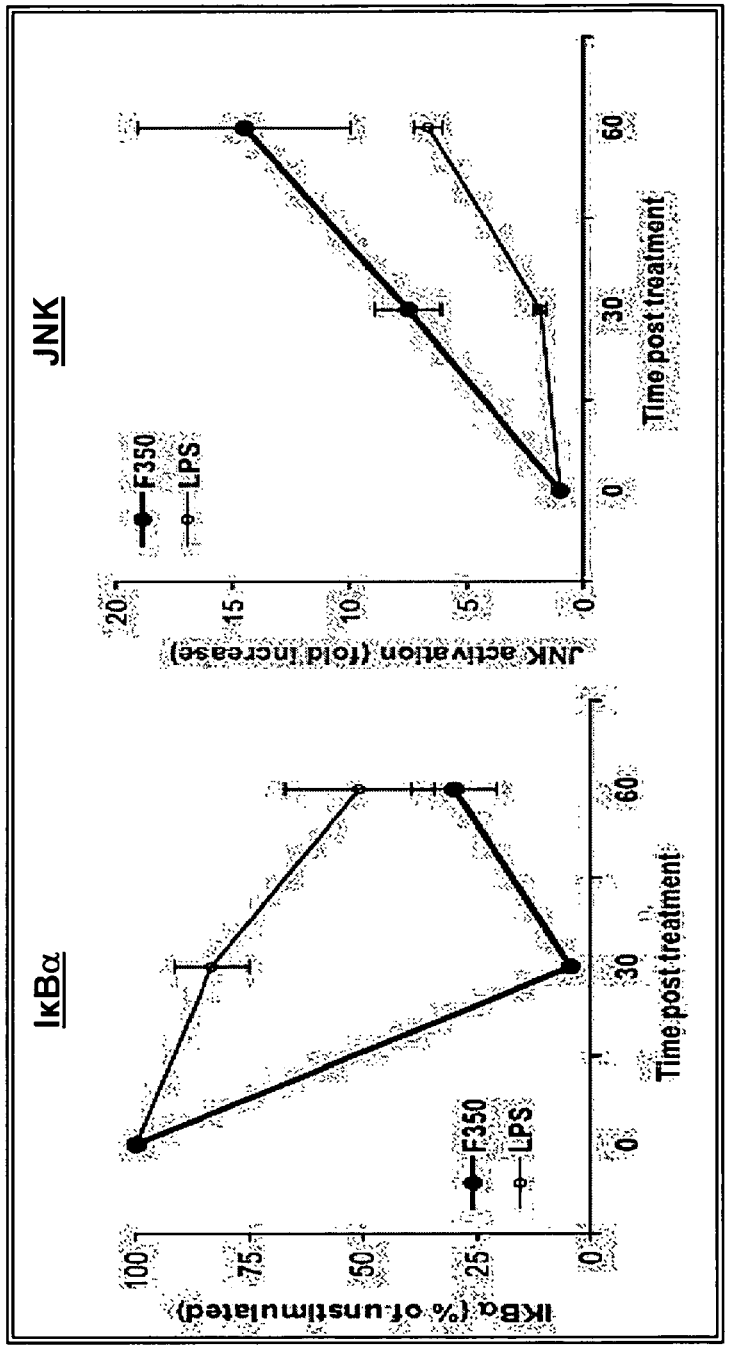
FIG. 4 shows that GAPDH (i.e., F350 in the figure) activates inflammatory signaling pathways through the TLR4 receptor in RAW264.7 macrophage-like cells.

RAW264.7 macrophage-like cells were challenged with either 50 μg/ml GAPDH or 20 ng/ml LPS in a time-course consisting of six time points ranging from 180 min to 0 min. After treatments were completed, the media was aspirated off and cell lysis buffer was applied to the cells. Protein assays were conducted on cell lysates in order to standardize the quantity of protein loaded into each well of SDSPAGE gels for separation. Gels were then transferred to PVDF membranes, and Western blot analysis was conducted on lysates from cells challenged with GAPDH or with LPS. As shown in FIG. 4, we found that GAPDH treatment activates the NF-κB and the JNK signaling pathways. In RAW264.7 macrophage-like cells challenged with LPS, the basal level of IκBα decreased over time, and slowly returned toward the base line, suggesting a transient activation of the NF-κB pathway. When RAW264.7 cells were challenged with GAPDH, the basal level of IκBα decreased dramatically and was nearly undetectable by 30 minutes post treatment, then slowly returned toward the base line. This nearly quantitative IκBα degradation suggests very potent activation of the NF-κB pathway at 30 minutes post GAPDH treatment.

In RAW264.7 cells, the basal activity of the JNK pathway was initially low. However, following LPS challenge JNK activation was rapidly stimulated, and after 30 minutes was increased by about a two-fold. Sixty minutes after LPS treatment, it was increased by about seven-fold. Interestingly, when the cells were treated with GAPDH, the levels of activated JNK increased at a much faster rate. 30 minutes after GAPDH challenge, we observed an approximately eight-fold increase in activated JNK levels, which rose to an approximately fifteen-fold increase after 60 minutes. These results indicate that GAPDH activates intracellular signaling pathways that are stimulated by inflammatory molecules such as PAMPs, DAMPs, and pro-inflammatory cytokines. These findings support the hypothesis that GAPDH is an endogenous mediator of inflammation that activates TLR4 signaling pathways.

The α-GAPDH #4418 Polyclonal Antibody Neutralizes GAPDH in Human Whole Blood Assays.

Figure 5:
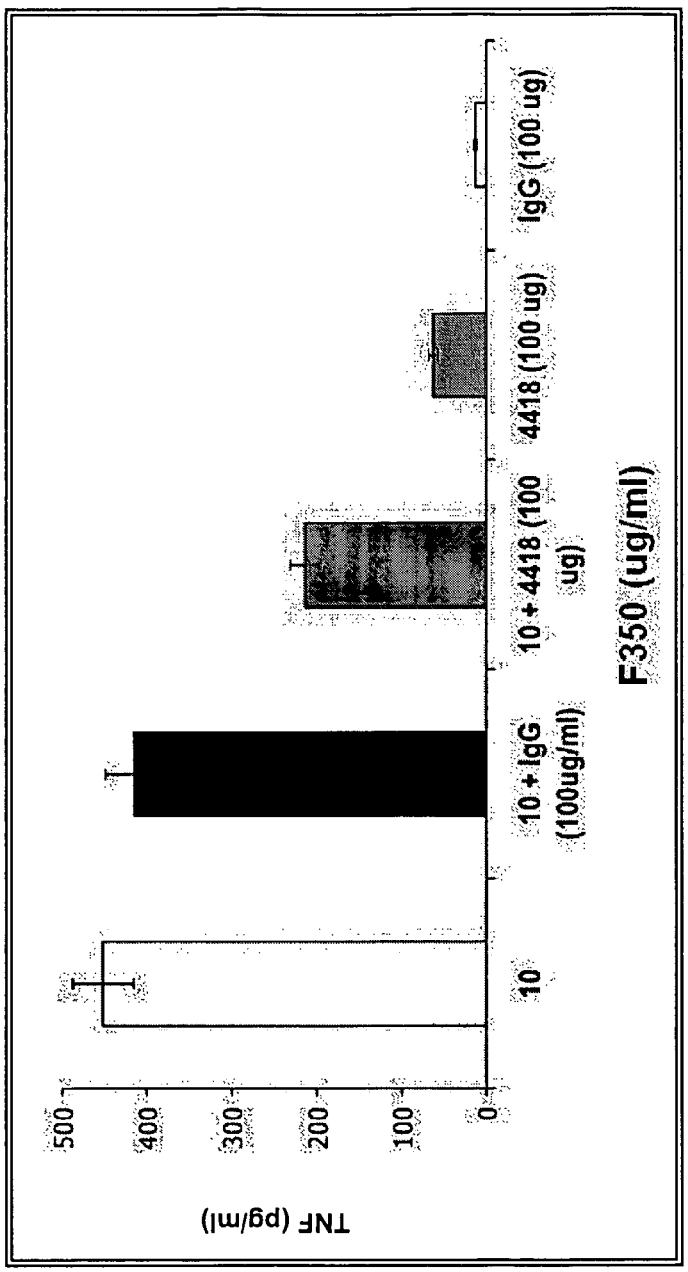
FIG. 5 shows that the $\alpha$-GAPDH #4418 polyclonal antibody (i.e., $\alpha$-F350 #4418 polyclonal antibody in the figure) neutralizes GAPDH (i.e., F350 in the figure) in human whole blood assays.
Figure 6:
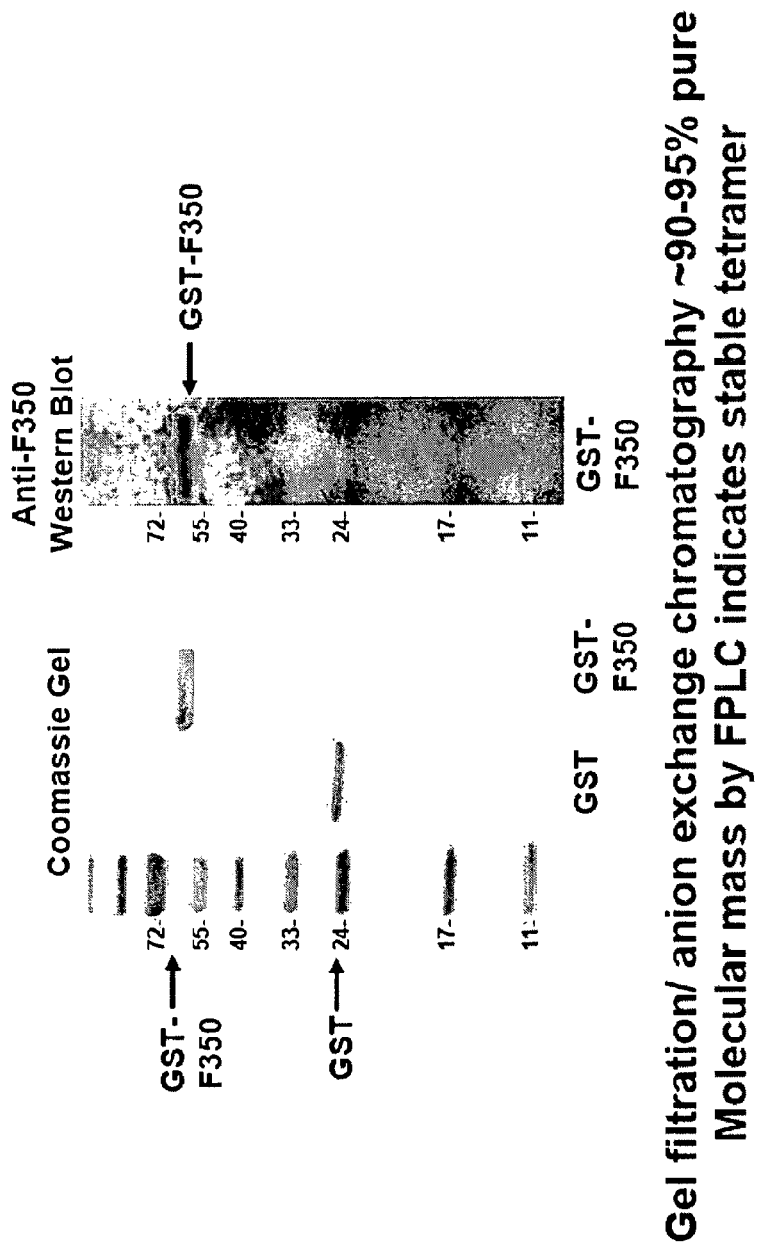
FIG. 6 shows that that the purified recombinant GST-GAPDH (i.e., GST-F350 in the figure) is a stable tetramer.
Figure 7:
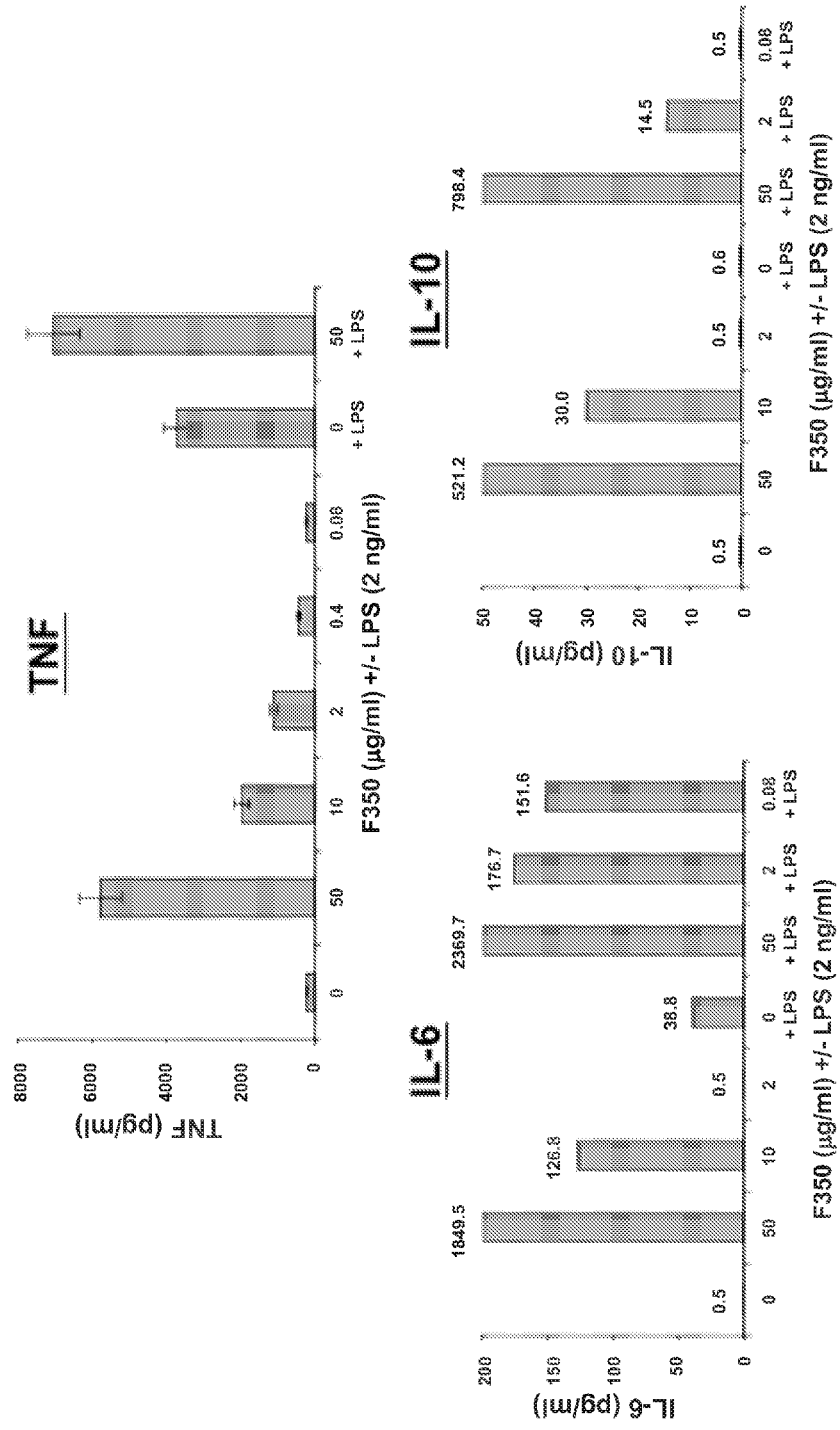
FIG. 7 shows that purified GST-GAPDH elicits inflammatory responses from cultured macrophages.
Figure 8:
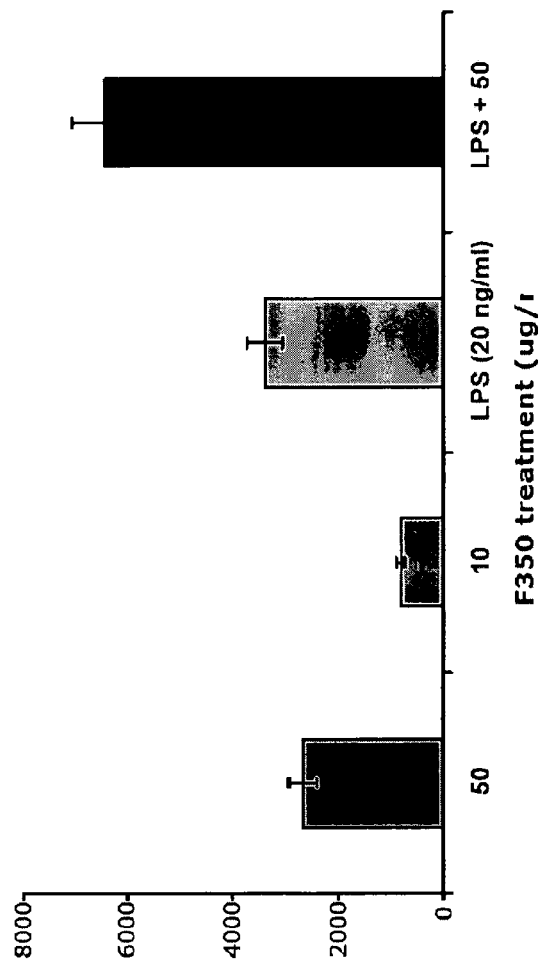
FIG. 8 shows that purified GST-GAPDH elicits an inflammatory cytokine reponse from human whole blood, and that the inflammatory response to GAPDH is synergistic with LPS.
Figure 9:
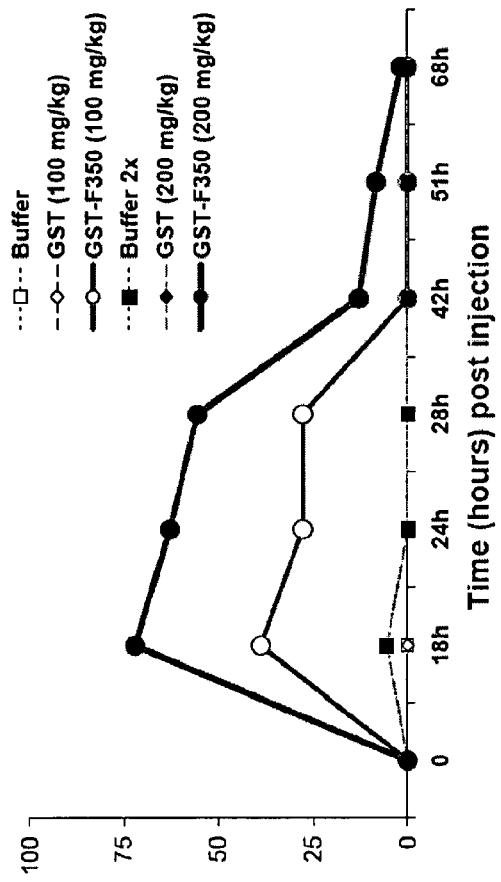
FIG. 9 shows that purified recombinant GST-GAPDH challenge causes sickness in mice.
Figure 10:
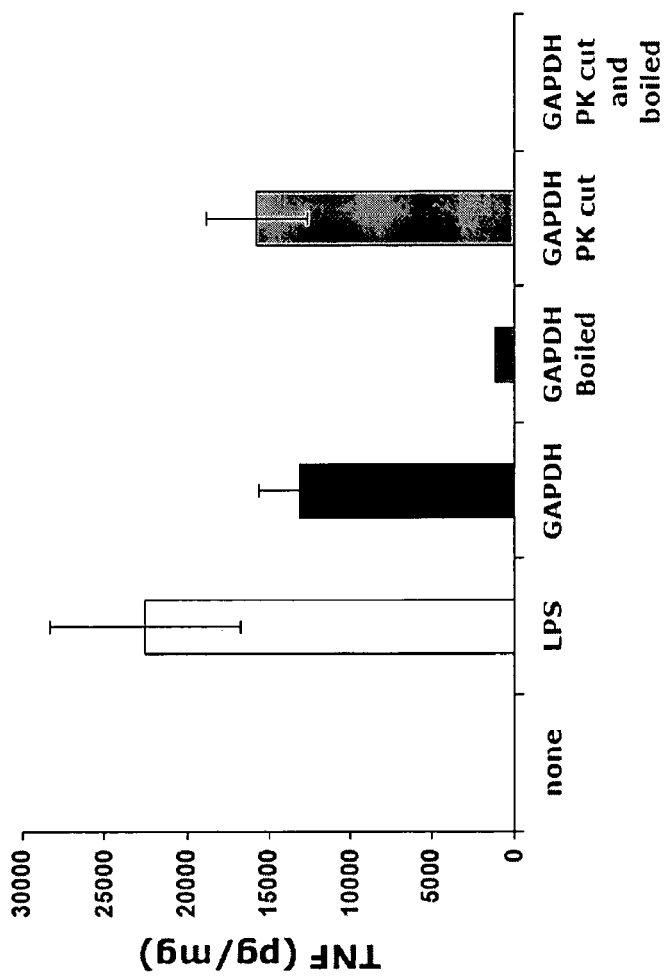
FIG. 10 shows that GAPDH inflammatory activity is maintained by proteolytic fragments.
Figure 11:
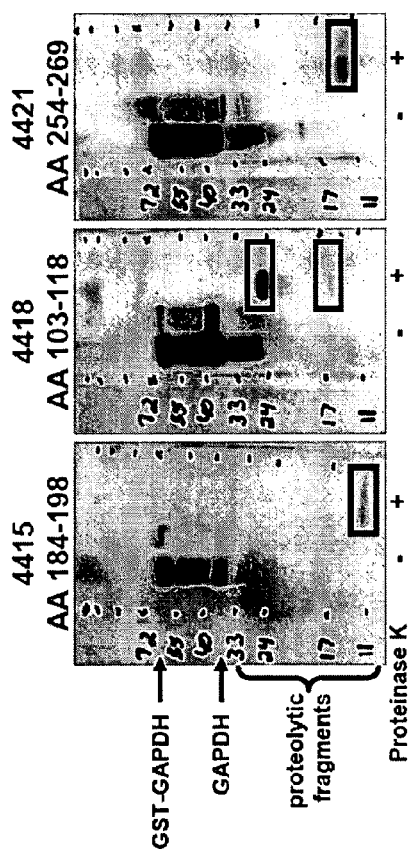
FIG. 11 also shows that GAPDH inflammatory activity is maintained by proteolytic fragments, and that the large fragments remain intact after proteinase K treatment.
Figure 12:
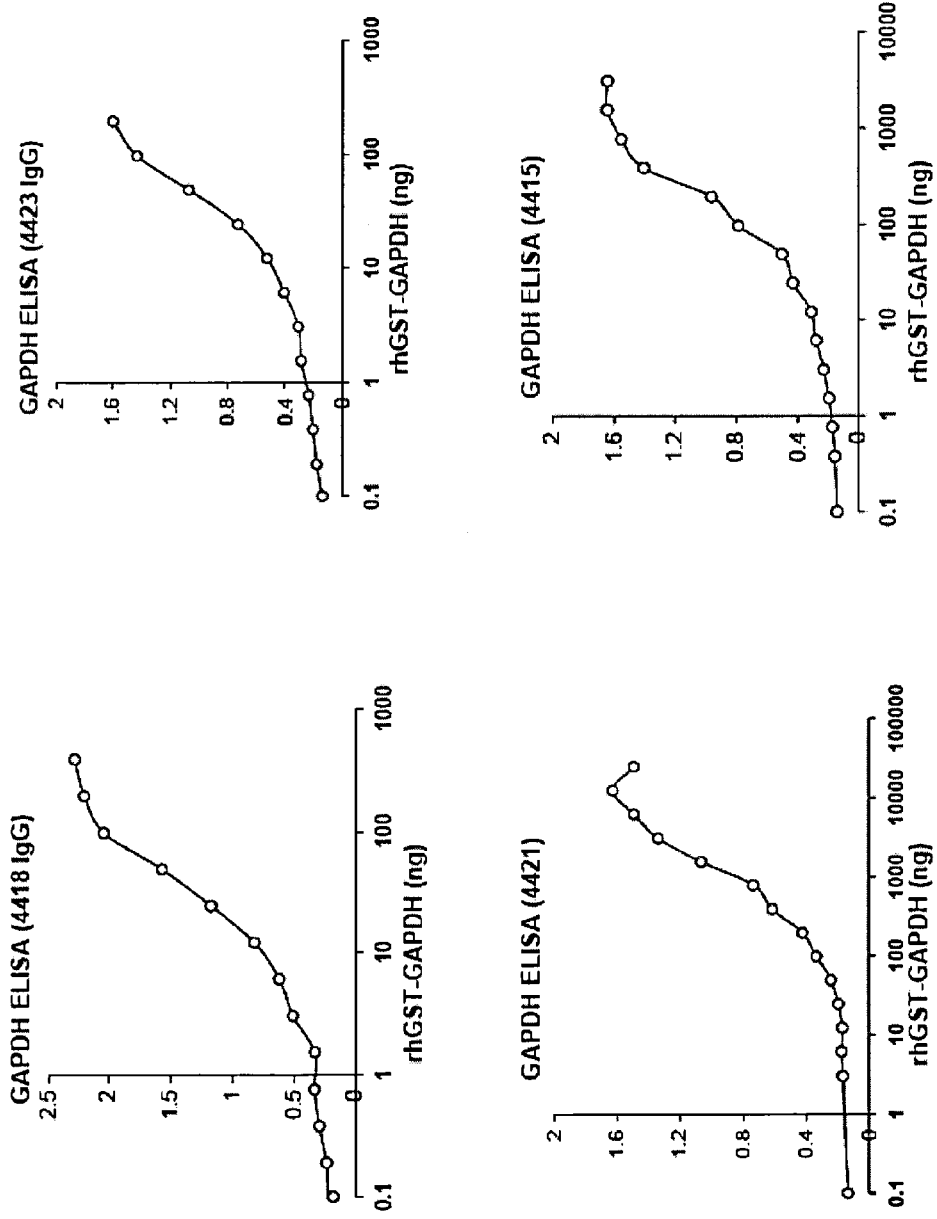
FIG. 12 shows that GAPDH antibodies function in capture ELISA.
Figure 13:
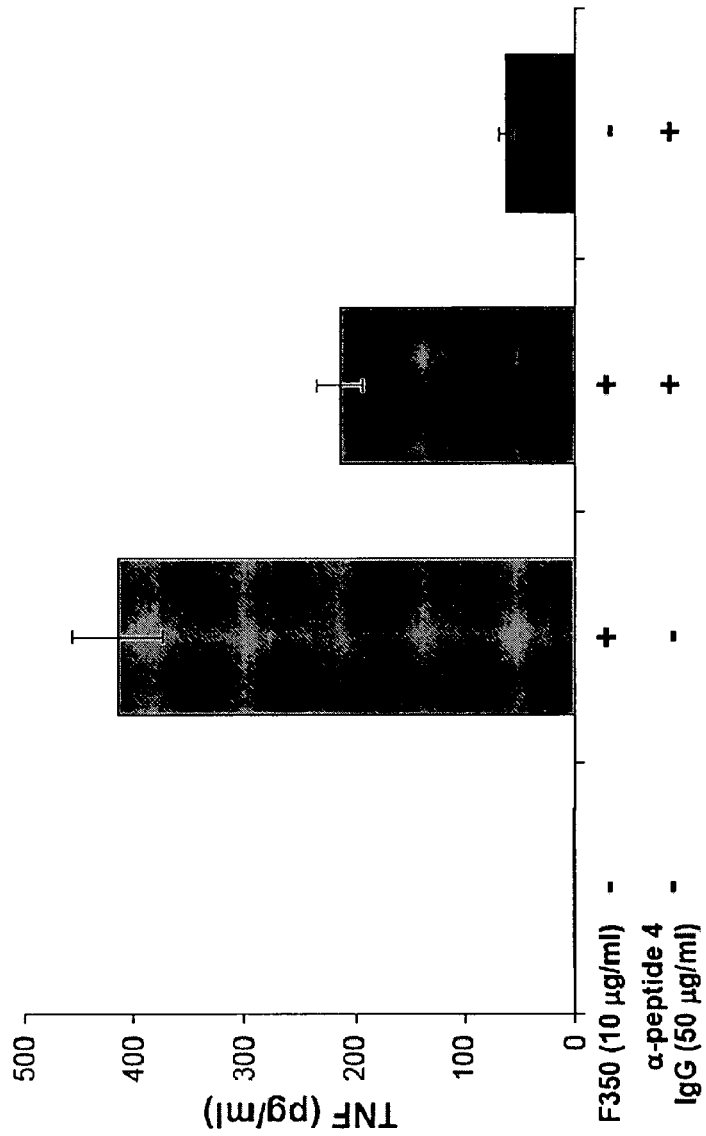
FIG. 13 shows that anti-GAPDH 4418 antibody is neutralizing in human whole blood assay.
Figure 14:
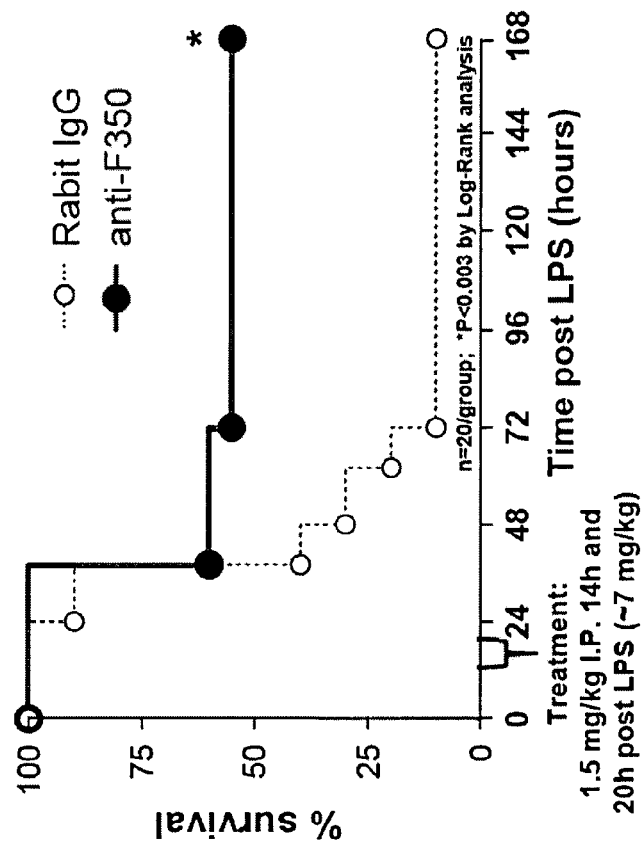
FIG. 14 shows that anti-GAPDH 4418 antibody improves survival during lethal endotoxemia in mice.
Figure 15:
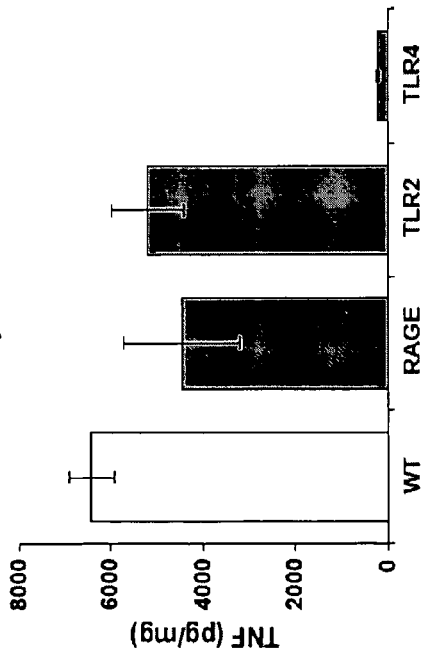
FIG. 15 shows that TLR4 KO macrophages do not respond to GAPDH (i.e., F350 in the figure).
Figure 16:
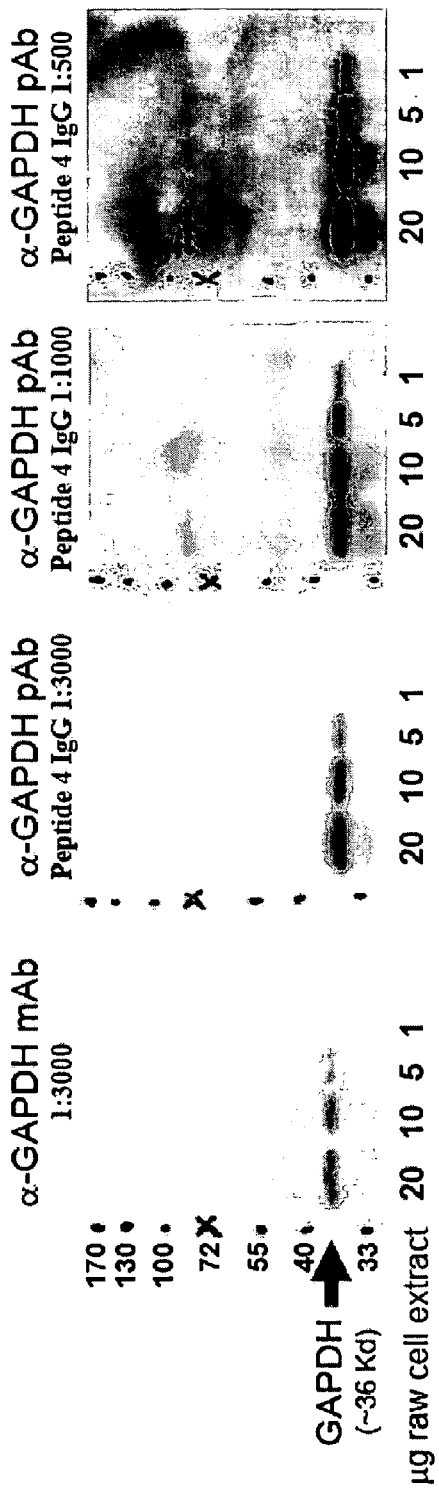
FIG. 16 shows that IgG from peptide 4 anti-serum (rabbit 4418) has high specificity and sensitivity against RAW cell extracts.

As previously noted, RAW264.7 macrophage-like murine cells challenged with GAPDH release pro-inflammatory cytokine mediators such as TNF and IL-6. Because we were ultimately interested in human inflammatory disease, we next tested whether GAPDH could also induce inflammatory responses from human whole blood ex vivo. We also used this assay system to test whether an antibody directed against GAPDH can neutralize its inflammatory activity in human whole blood. As shown in FIG. 5, purified recombinant GAPDH elicits a strong TNF response from human whole blood. Four hours after GAPDH treatment, samples were collected and plasma was separated by centrifugation. Plasma TNF levels were then measured by ELISA, showing that a 10 μg/ml F350 challenge yielded approximately 450 pg/ml TNF. We next pre-treated the purified recombinant GAPDH with purified IgG from α-GAPDH #4418 antiserum. This mixture was then applied to the whole blood. Pre-treatment of GAPDH with α-GAPDH #4418 reduced the TNF levels elicited from human whole blood challenged with GAPDH by approximately 50%. However, the α-GAPDH #4418 antibody was not affinity purified, and only a small percentage of the total IgG from the rabbit antiserum is directed against GAPDH. Therefore, we hypothesize that an affinity-purified antibody would give a stronger neutralization. The ability of the α-GAPDH #4418 antibody to neutralize GAPDH inflammatory activity is an important observation because it indicates the validity of GAPDH as a therapeutic target in human inflammatory disease.

The blood samples treated with the α-GAPDH #4418 antibody alone produced about 60 pg/ml TNF. The α-GAPDH #4418 antibody was tested for LPS contamination by Limulus Amoebocyte Lysate Assay (LAL), and it was found to contain between 8 and 20 pg LPS/mg protein (data not shown). This is a likely contribution to the TNF response in the blood treated only with the α-GAPDH #4418 antibody. Note that unstimulated whole blood typically does not contain detectable TNF (data not shown).

Additional Experiments.

Additional experiments were conducted and the results of these experiments are presented in FIGS. 6-17. Of note, purified GST-GAPDH was found to elicit inflammatory cytokine response from human blood and the inflammatory response to GAPDH was synergistic with LPS (see, FIG. 8). In addition, the purified recombinant GST-GAPDH challenge was found to cause sickness in mice based on an evaluation of certain clinical scoring parameters (i.e., piloerection, closed eyes, diarrhea, tremoring, activity, relative temperature (9 point maximum/mouse; n=6/group)) (see, FIG. 9). The GAPDH inflammatory activity also was found to be maintained by proteolytic fragments (see, FIGS. 10 and 11). In additional experiments, the anti-GAPDH 4418 antibody was found to be neutralizing in a human whole blood assay (see, FIG. 13) and administration of the anti-GAPDH 4418 antibody was found to improve survival during lethal endotoxemia in mice (see, FIG. 14).

CONCLUSION

Current therapies for sepsis are largely ineffective. The onset of sepsis can occur very rapidly, and may be unbeknownst to the patient. Biologically, the "cytokine cascade" is just beginning, mounting the body's immune system to respond to the perceived trouble (i.e. infection, trauma, injury). By the time the patient recognizes that he or she is ill, the early pro-inflammatory mediators like TNF and IL-1 have already run their course; to target them would be ineffective [1,10-12, 18, 19]. However, late mediators of pathological inflammation, such as HMGB1, may not have been elicited yet from immune cells. However, HMGB1 poses a difficult situation, as it is also involved in promoting wound healing and in the resolution of inflammation. To reduce its ability to function may be detrimental to the organism if it is inappropriately targeted. Therefore, it is important to identify novel late mediators of inflammation, such as GAPDH, which may not be as pleiotropic as HMGB1 in their scope of activities.

We have shown that GAPDH can function as a mediator of inflammation. Innate immune cells treated with endotoxin respond by releasing cytokines to increase the body's response to the pathogen. We found that GAPDH is released between 16 and 18 hours post endotoxin treatment in murine macrophage-like RAW264.7 cells. Inflammatory cytokines elicit more inflammatory cytokines and other mediators of inflammation from immune cells. This was true in the case of GAPDH; when GAPDH treatments were applied to RAW264.7 cells, the cells responded by producing TNF and IL-6, two pro-inflammatory cytokines. Inflammatory cytokines use intracellular signal transduction pathways to induce immune cells to respond appropriately. IκBα degradation and JNK activation are molecular markers of inflammatory pathway stimulation by molecules that promote inflammation (i.e. PAMPs, DAMPs, pro-inflammatory cytokines). GAPDH treatment resulted in both the degradation of IκBα and the activation of JNK in lysates from RAW264.7 macrophage-like cells, indicating that it can stimulate inflammatory pathway signaling. Interestingly, the ability of GAPDH to elicit cytokines from macrophages was dependent on the TLR4 receptor, a pattern recognition receptor that has been implicated in the inflammatory activity of other endogenous mediators such as HMGB1 [26].

In additional experiments, purified recombinant GST-GAPDH challenge was shown to cause sickness in mice, further supporting the role that GAPDH may play in the lethal progression of pathogenic inflammation. Significantly, a polyclonal antibody generated against GAPDH (i.e., the anti-GAPDH 4418 antibody) was found to be neutralizing in a human whole blood assay, and administration of the anti-GAPDH 4418 antibody was found to improve survival during lethal endotoxemia in mice. This demonstrates that GAPDH is useful as a therapeutic target to improve the clinical outcome in inflammatory disease, and that GAPDH inhibitors are potentially useful for the treatment of inflammatory disease, such as sepsis and related conditions.

REFERENCES

1. Tracey, K. J. (2002). The inflammatory reflex. *Nature* 420, 853-859.
2. Ulloa, L. & Tracey, K. J. (2005). The 'cytokine profile': A code for sepsis. *Trends in Molecular Medicine* 11(2), 56-63.
3. Martin, G. S., Mannino, D. M., Eaton, S., & Moss, M. (2003). The epidemiology of sepsis in the United States from 1979 through 2000. *The New England Journal of Medicine* 348, 1546-1554.
4. Parrish, W. R., Gallowitsch-Puerta, M., Czura, C. J., & Tracey, K. J. (In Press). Experimental therapeutic strategies for severe sepsis: Mediators and mechanisms. *Annals of the New York Academy of Sciences*.
5. Tracey, K. J. (2005). *Fatal Sequence: The Killer Within*. Dana Press, distributed by The University of Chicago.
6. Marshall, J. C., Cook, D. J., Christou, N. V., Bernard, G. R., Sprung, C. L., & Sibbald, W. J. (1995). Multiple organ dysfunction score: a reliable descriptor of a complex clinical outcome. *Critical Care Medicine* 23, 1638-1652.
7. Riedemann, N. C., Guo, R. F., & Ward, P. A. (2003). Novel strategies for the treatment of sepsis. *Nature Medicine* 9, 517-524.
8. Tracey, K. J., Fong, Y., Hesse, D. G., Manogue, K. R., Lee, A. T., Kuo, G. C., Lowry, S. F., & Cerami, A. (1987). Anti-cachectin/TNF monoclonal antibodies prevent septic shock during lethal bacteraemia. *Nature* 330, 662-664.
9. Tracey, K. J., Beutler, B., Lowry, S. F., Merryweather, J., Wolpe, S., Milsark, I. W., Hariri, R. J., Fahey, T. J., Zantella, A., Albert, J. D., et al. (1986). Shock and tissue injury induced by recombinant human cachectin. *Science* 234, 470-474.
10. Wang, H., Bloom, O., Zhang, M., Vishnubhakat, J. M., Ombrellino, M., Che, J., Frazier, A., Yang, H., Ivanova, S., Borovikova, L., Manogue, K. R., Faist, E., Abraham, E., Andersson, J., Andersson, U., Molina, P. E., Abumrad, N. N., Sama, A., & Tracey, K. J. (1999). HMG-1 as a late mediator of endotoxin lethality in mice. *Science* 285, 248-251.
11. Tracey, K. J. & Abraham, E. (1999). From mouse to man: Or what have we learned about cytokine-based anti-inflammatory therapies? *Shock* 11, 224-225.
12. Andersson, U., Wang, H., Palmblad, K., Aveberger, A. C., Bloom, O., Erlandsson-Harris, H., Janson, A., Kokkola, R., Zhang, M., Yang, H., & Tracey, K. J. (2000). High mobility group 1 protein (HMG-1) stimulates proinflammatory cytokine synthesis in human monocytes. *The Journal of Experimental Medicine* 192, 565-570.
13. Ferrara, J. L., Abhyankar, S., & Gilliland, D. G. (1993). Cytokine storm of graft-versus-host disease: A critical effector role for interleukin-1. *Transplantation Proceedings* 25 (1 Pt 2), 1216-1217.

14. Giroir, B. P. (1993). Mediators of septic shock: New approaches for interrupting the endogenous inflammatory cascade. *Critical Care Medicine* 21(5), 780-789.
15. Parrish, W. R. & Ulloa, L. (2007). High-mobility group box-1 isoforms as potential therapeutic targets in sepsis. *Methods in Molecular Biology* 361, 145-162.
16. Mantell, L. L., Parrish, W. R., & Ulloa, L. (2006). HMGB-1 as a therapeutic target for infectious and inflammatory disorders. *Shock* 25(1), 4-11.
17. Straino, S., Di Carlo, A., Mangoni, A., De Mori, R., Guerra, L., Maurelli, R., Panacchia, L., Di Giacomo, F., Palumbo, R., Di Campli, C., Uccioli, L., Biglioli, P., Bianchi, M. E., Capogrossi, M. C., & Germani, A. (2008). High-mobility group box 1 protein in human and murine skin: involvement in wound healing. *The Journal of Investigative Dermatology* 128(6), 1545-1553.
18. Ulloa, L., Ochani, M., Yang, H., Tanovic, M., Halperin, D., Yang, R., Czura, C. J., Fink, M. P., & Tracey, K. J. (2002). Ethyl pyruvate prevents lethality in mice with established lethal sepsis and systemic inflammation. *Proceedings of the National Academy of Sciences of the United States of America* 99, 12351-12356.
19. Wang, H., Yang, H., Czura, C. J., Sama, A. E., & Tracey, K. J. (2001). HMGB1 as a late mediator of lethal systemic inflammation. *American Journal of Respiratory and Critical Care Medicine* 164, 1768-1773.
20. Czura, C. J., Yang, H., & Tracey, K. J. (2003). High mobility group box-1 as a therapeutic target downstream of tumor necrosis factor. *The Journal of Infectious Diseases* 187, S391-S396.
21. Lu, Y. C., Yeh, W. C., & Ohashi, P. S. (2008). LPS/TLR4 signal transduction pathway. *Cytokine* 42(2), 145-151.
22. Akira, S., Uematsu, S., & Takeuchi, O. (2006). Pathogen recognition and innate immunity. *Cell* 124, 783-801.
23. Lee, H. K. & Iwasaki, A. (2007). Innate control of adaptive immunity: Dendritic cells and beyond. *Seminars in Immunology* 19, 48-55.
24. Takeda, K. & Akira, S. (2004). TLR signaling pathways. *Seminars in Immunology* 16, 3-9.
25. Foell, D., Wittkowski, H., & Roth, J. (2007). Mechanisms of disease: a 'DAMP' view of inflammatory arthritis. *Nature Clinical Practice Rheumatology* 3(7), 382-390.
26. Yu, M., Wang, H., Ding, A., Golenbock, D. T., Latz, E., Czura, C. J., Fenton, M. J., Tracey, K. J., & Yang, H. (2006). HMGB1 signals through toll-like receptor (TLR) 4 and TLR2. *Shock* 26(2), 174-179.
27. Ebersole, J. L. Cappelli, D. (2000). Acute-phase reactants in infectious and inflammatory diseases. *Periodontology* 23, 19-49.

What is claimed is:

1. A method of treating a subject having a condition mediated by an inflammatory cytokine cascade comprising administering to the subject an anti-glyceraldehyde 3-phosphate dehydrogenase (GAPDH) antibody in an amount effective to reduce the level of one or more biomarkers that are elevated in a condition mediated by the inflammatory cytokine cascade, wherein the one or more biomarkers are selected from the group consisting of tumor necrosis factor (TNF), interleukin 6 (IL-6), and interleukin 10 (IL-10), and wherein the condition is selected from the group consisting of sepsis, septicemia and endotoxic shock.
2. The method of claim 1, wherein the antibody is a polyclonal or monoclonal antibody.
3. The method of claim 1, wherein the antibody is a humanized or a human antibody.
4. The method of claim 1, wherein the condition is sepsis.
5. The method of claim 1, wherein the condition is septicemia.
6. The method of claim 1, wherein the condition is endotoxic shock.
7. The method of claim 1, wherein the anti-GAPDH antibody reduces the level of TNF in the blood.
8. A method of treating sepsis, septicemia and/or endotoxic shock in a subject comprising administering to the subject an anti-glyceraldehyde 3-phosphate dehydrogenase (GAPDH) antibody in an amount effective to treat sepsis, septicemia and/or endotoxic shock.
9. The method of claim 8, wherein the antibody is a polyclonal or monoclonal antibody.
10. The method of claim 8, wherein the antibody is a humanized or a human antibody.
11. The method of claim 8, wherein the subject has sepsis.
12. The method of claim 8, wherein the subject has septicemia.
13. The method of claim 8, wherein the subject has endotoxic shock.
14. The method of claim 8, wherein sepsis is treated.
15. The method of claim 8, wherein septicemia is treated.
16. The method of claim 8, wherein endotoxic shock is treated.

\* \* \* \* \*